United States Patent [19]

Owens

[11] 4,217,890
[45] Aug. 19, 1980

[54] SURGICAL SLING FOR POSITIONING A HARVESTED KIDNEY DURING SURGICAL REATTACHMENT

[76] Inventor: Milton L. Owens, 128 20th St., Manhattan Beach, Calif. 90266

[21] Appl. No.: 957,569

[22] Filed: Nov. 3, 1978

[51] Int. Cl.³ .............. A61B 19/00; A61B 17/00; B65D 30/00; B65D 33/00
[52] U.S. Cl. .............. 128/1 R; 128/303 R; 229/53
[58] Field of Search ........... 128/335.5, 334 R, 1 R, 128/303 R; 229/53; 62/371

[56] References Cited

U.S. PATENT DOCUMENTS

| 2,143,910 | 1/1939 | Didusch | 128/335 |
|---|---|---|---|
| 2,835,253 | 5/1958 | Borgeson | 128/303 R |
| 3,111,943 | 11/1963 | Orndorff | 128/303 R |
| 3,490,438 | 1/1970 | Lavender | 128/1 R |
| 3,552,637 | 1/1971 | Swinford | 229/53 |
| 3,556,389 | 1/1971 | Gregoire | 229/53 |
| 3,605,747 | 9/1971 | Pashkow | 128/303 R |
| 3,777,507 | 12/1973 | Burton et al. | 128/1 R |
| 3,810,367 | 12/1974 | Peterson | 62/371 |
| 3,827,251 | 8/1974 | Koski et al. | 128/1 R |
| 3,952,536 | 4/1976 | Faust et al. | 62/371 |
| 3,983,863 | 10/1976 | Janke et al. | 128/1 R |
| 4,113,169 | 9/1978 | Carlisle | 229/53 |

FOREIGN PATENT DOCUMENTS

| 279888 | of 1971 | U.S.S.R. | 128/334 R |
|---|---|---|---|
| 506399 | of 1976 | U.S.S.R. | 128/334 R |
| 545312 | of 1977 | U.S.S.R. | 128/1 R |

Primary Examiner—Robert W. Michell
Assistant Examiner—C. W. Shedd
Attorney, Agent, or Firm—Elliott N. Kramsky

[57] ABSTRACT

A method and associated surgical apparatus adapted to minimize the deterioration of kidney function incurred during transplantation by warm ischemia. A sling of non-wettable insulative material is employed by the surgical assistant to contain the harvested kidney. The sling conforms generally to the shape of the kidney. A suitably located aperture is provided so that arterial, venous and ureteral (anastomosis) linkages can be surgically performed while rewarming of the enclosed kidney is substantially inhibited.

6 Claims, 4 Drawing Figures

SURGICAL SLING FOR POSITIONING A HARVESTED KIDNEY DURING SURGICAL REATTACHMENT

BACKGROUND OF THE INVENTION

1. Field of the Invention

The present invention relates to surgical methods and associated apparatus therefor. More particularly, it relates to methods and means substantially directed to achieving improved kidney function in association with present day surgical transplantation technique.

2. Description of the Prior Art

Present day transplantation of the human kidney occurs in three qualitatively distinct stages. The first, sometimes referred to as "harvesting" involves the surgical removal of the kidney from the donor. It is during this stage that the kidney's blood supply is removed. Harvesting is followed by a storage-transport stage. During the storage-transport stage, the kidney must be maintained in a condition of hypothermia (below body temperature, 38° C.) to decrease the oxygen needs of the organ. It has been found that significant deterioration of kidney function (warm ischemia) occurs when the kidney is maintained without blood supply at a temperature greater than 18° C. Significantly, the cortex of the kidney, the location of the important urine filtration function, is located exteriorly and thus is particularly subject to warm ischemia when held in the surgeon's hand or against the donee's tissues.

Various methods have been employed, and meet with relative success for maintenance of the harvested kidney at adequate hypothermia for periods of up to forty-eight hours of time during the second or storage-transport stage. These include, but are not limited to, the (pumped) circulation of a cold solution (5°-15° C.) such as cryo-precipitated plasma and the storage of the kidney in a 0° C. (ice) equilibrium bath of an intra or extra cellular electrolyte solution.

During the third stage, surgical re-implantation, the kidney is commonly held (positioned) by an assisting physician while the operating surgeon attaches the renal vein and artery and the ureter, a tube which carries the purified (filtered) urine to the bladder from the cortex of the kidney. This surgical procedure (or anastomosis) may be accomplished in about forty-five minutes, leaving the kidney with a new blood supply (the donee's) even as the suturing of the donee's surgical cavity incision proceeds.

It is during the period of time that the kidney is being surgically connected to the donee's blood supply that kidney deterioration due to warm ischemia takes place. This results from the fact that manual positioning of the harvested kidney, removed from the above-mentioned temperature preservative means of the storage-transport stage, is required by present surgical techniques. The kidney is at this time removed from all artificial storage-transport cooling systems and, having no functioning blood supply, subject to the effects of warm ischemia for the above-mentioned period of approximately forty-five minutes. The degree of deterioration of kidney function which takes place at this time is a direct function of the amount of rewarming that occurs. The success of the transplant will depend substantially upon the damage necessarily incurred by the transplanted kidney during anastomosis.

SUMMARY AND OBJECTS OF THE INVENTION

It is therefore an object of the present invention to provide a method and means for minimizing the amount of warm ischemia incurred by a harvested kidney during anastomosis.

Another object of the invention is to achieve the above object by employing a means to aid the surgical assistant in the positioning of the harvested kidney during anastomosis.

Yet another object of the invention is to achieve the above object by employing means which do not complicate the surgical procedure of reimplantation nor increase the risks associated therewith.

To achieve these and other objects there is provided by the present invention a sack or sling of impermeable insulative material. The sling is two-sided, formed in substantial accordance with the shape of a kidney, having an aperture in the inferior portion therefor and handle means formed at the superior portion. The aperture allows the protrusion of the ureter and the renal vein and artery for surgical attachment to the donee's system. The handle provides a means for the surgical assistant to position the kidney while the kidney is surrounded by the insulative material. Uncoupling means is incorporated within the sling to allow the assistant to uncouple the kidney from the sling once the donee's blood supply has been surgically joined to the kidney.

These and other objects and advantages of the invention will be described in greater detail by reference to the drawings in which.

Figure 3:
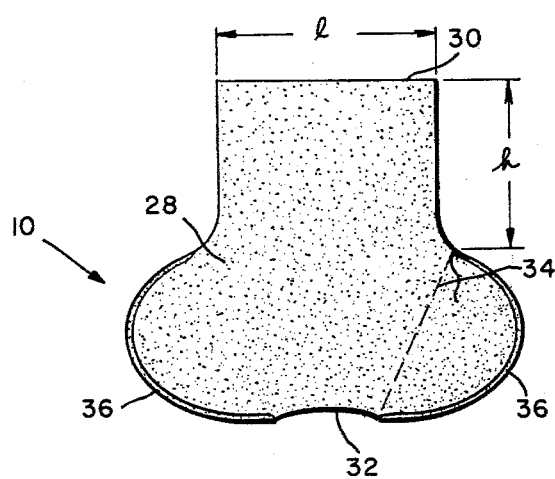
Figure 4:
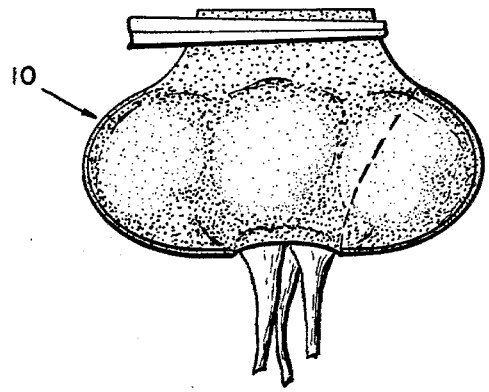

FIG. 3 is an illustration of the surgical sling 10 of the present invention showing a detailed view of one side 28 thereof; and FIG. 4 is a side view of the sling 10 of the present invention being grasped with the aid of a clamp.

DESCRIPTION OF THE PREFERRED EMBODIMENT

Figure 1:
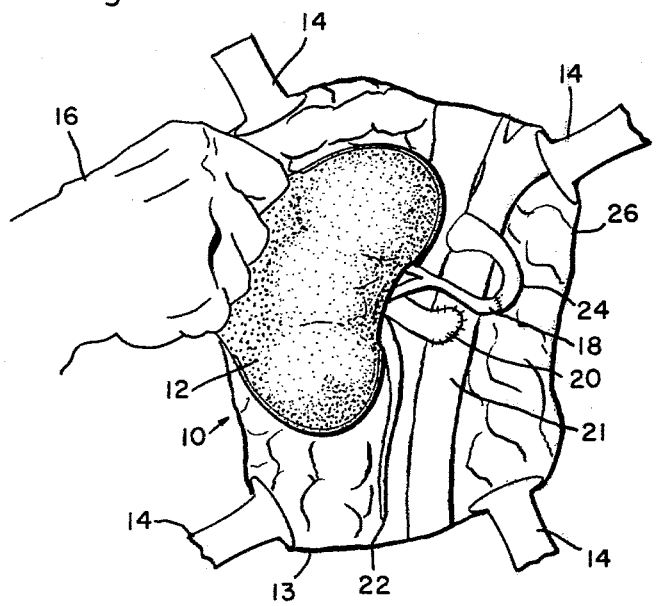
FIG. 1 is an illustration of the utilization of the sling of the present invention during anastomosis.
Figure 2:
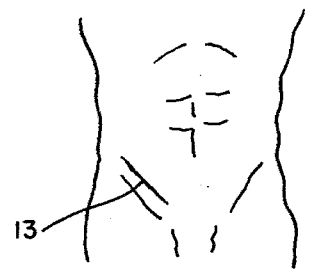
FIG. 2 is an illustration of the implantation incision principally to aid in an understanding of the surgical cavity of FIG. 1.

There is shown in FIG. 1 the surgical sling 10 of the present invention employed in the process of implantation of a harvested kidney 12. One may gain an appreciation of the relative location of the surgical working area by reference to FIG. 2, which shows the location of the incision 13 for implantation of the right kidney in the lower abdomen. It may be noted that the position of the transplanted kidney varies somewhat from the normal position of the organ, an anatomical fact reflecting surgical choices and having no bearing on the significance of the present invention.

Returning again to FIG. 1, it is seen that clamps or retractors 14 engage the edges of the incision 13 to create the cavity which constitutes the surgical working space. Commonly such an area will measure 15 cm by 10 cm based upon an incision of approximately 20 cm. The sling 10, having kidney 12 therein, is held for the operating surgeon by an assistant. In FIG. 1, the assistant has grasped the sling 10 by his hand 16. Handle means employed therefor constitute a significant feature of the present invention, although obstructed from direct view by the hand 16 of the assistant. As an alternative to the method employed in FIG. 1 by the surgical assistant, the sling 10 may be indirectly grasped and held during surgery by means of an hemostatic clamp or its equivalent.

Protruding from the bottom of the sling are the renal artery 18, the renal vein 20 and the ureter 22. The renal artery 18 carries oxygenated blood from the heart to the kidney 12 and will be surgically attached to the iliac artery 24 of the donee. The renal vein 20, which returns the post-metabolized blood from the kidney 12 to the lungs is attached to the iliac vein 21 while the ureter 22, when attached to the bladder serves as the conduit of the urine formed by filtration of blood by the kidney.

FIG. 3 illustrates the sling 10 of the invention in greater detail. The sling 10 is comprised of two (matching) sides, each resembling the side 28, allowing the sling 10 to be stored flat for convenience. Each side 28 is shaped to approximate the shape of the kidney. A tab 30 is formed therewith at the superior portion of the side 28 to serve as the "handle" of the sling 10. The tab 30, as mentioned above in conjunction with FIG. 1, provides a means for the surgical assistant to grasp the sling 10 directly (manually) or indirectly (clamp) while neither traumatizing the enclosed kidney nor interfering with the surgical implantation work area. Its length, l, is chosen so that the harvested kidney may be placed into the sling 10 through "peeled back" tabs 30, without necessitating a traumatizing degree of temporary deformation during passage therethrough. The height, h, of the tab 30 is sufficient to allow the surgical assistant to grasp the sling comfortably. If, for instance, the height h were relatively skimpy, an assistant having large hands would be forced to use a clamping procedure as shown in FIG. 4, rather than the manual grasping of FIG. 1, during surgery. Adequate tab 30 height h allows the choice of either mode, as preferred.

An aperture 32 is provided in the approximate middle of the inferior portion of the side 28 to allow the above noted protrusion of ureter, renal vein and artery during implantation. A tear strip 34 is embedded in each side 28. The tear strip 34 or equivalent mechanism runs from the edge of the aperture 32 to the junction of the tab 30 with the sling 10. This serves as a convenient means for the release of the kidney from the sling 10 once the donee's blood supply has been attached. Each tear strip 34 may be pulled by either the surgical assistant or another aide once the kidney has been positioned in the cavity in preparation for resuturing the incision 13. The sling 10, after the pulling of the tear strip 34, comprises two unattached portions which may be easily removed from the surgical work area without contamination thereof.

Each side 28 of the sling is formed of an insulative impermeable material. Ethafoam, a registered trademark of the Dow Chemical Company has been utilized in the fabrication of a surgical sling 10 which has been successfully tested. This odorless product is a closed-cell polyethylene characterized by a high resistivity to chemicals and solvents and a very low water vapor transmission rate and comes in a wide range of densities. Other equivalent materials having substantially similar qualities are anticipated and envisioned within the scope of the present invention. The sides are joined together by a stamping and/or heat sealing process along the seam 36 which preserves the above-mentioned properties of the material along the junction of the sides.

The substantial benefit of the method and apparatus of the present invention in terms of reduced warm ischemia during kidney transplantation can be seen from the following data:

| Site (Source) | Insulation | Time: Ave | S.D. | No |
|---|---|---|---|---|
| Cortex (Human) | No | 13.8 | 2.7 | 5 |
| Cortex (Human) | Yes | 4.7 | .98 | 3 |
| Medulla (Human) | No | 9.8 | 1.9 | 6 |
| Medulla (Human) | Yes | 4.0 | .36 | 3 |
| Cortex (Dog) | No | 18.0 | .50 | 4 |
| Cortex (Dog) | Yes | 5.8 | 1.9 | 5 |
| Medulla (Dog) | No | 14.6 | 1.6 | 3 |
| Medulla (Dog) | Yes | 3.7 | 1.1 | 6 |

The above statistical data was gathered from cold stored (4° C.) human and canine kidneys which were rewarmed under conditions simulating a transplant. Intrarenal temperatures were monitored with thermistor probes. The "Time:Ave" data column represents equivalent minutes at 38° C. using published time-renal temperature relationships. It may be seen from the above data that an insulating sling according to the present invention decreases the equivalent amount of time ex vivo at 38° C. (warm ischemia) by a factor of three, indicating a dramatic reduction in the deterioration of function one might anticipate during the implantation stage.

Thus, it is seen that there has been provided by the present invention a method and apparatus which conveniently and significantly aids the kidney transplantation process by providing a simple yet effective sling peculiarly designed for enclosure of the harvested kidney during surgical implantation. The sling minimizes the damage necessarily resultant from warm ischemia.

What is claimed is:

1. A kidney sling for positioning a harvested kidney during surgical reattachment of said harvested kidney to a blood supply which comprises:
    a. a matching pair of continuous sling sides, each of said sling sides being formed of a substantially flat, thermally insulative and water-impermeable material substantially shaped at its periphery to conform closely to the shape of a kidney;
    b. said sides being joined together at their periphery to thereby form a sling having an interior cavity which closely conforms to the shape of a kidney; and
    c. an aperture formed in the lower portion of said sling to allow the protrusion of the artery, vein and ureter associated with said harvested kidney whereby said sling provides a thermally insulative environment for said kidney during such surgical reattachment process so that the effects of warm ischemia are minimized.

2. A surgical sling as defined in claim 1 wherein said sling additionally includes a tab, said tab being formed in the upper portion thereof and providing a means for holding said sling.

3. A surgical sling as defined in claim 2 additionally comprising means for disengaging said sling from said kidney after the reattachment thereof to a supply of blood.

4. A surgical sling as defined in claim 3 wherein said means for disengaging said sling from an enclosed kidney comprises a tear strip embedded in a portion of each sling side and extending substantially from said lower aperture to said tab.

5. In the transplantation of a kidney from a donor to a donee wherein it is required that the donor's supply of blood be removed from said kidney prior to the surgical attachment of said kidney to the blood supply of said donee, the improvement comprising the step of enclosing said harvested kidney in a sling fabricated of an impermeable, thermally insulative material, whereby the thermal insulation provides protection for said kidney during surgical attachment to the blood supply of said donee and warm ischemia during anastomosis is thereby minimized.

6. The transplantation of a kidney according to the method defined in claim 5 additionally characterized by the thermal insulation of said kidney by its enclosure in a sling of substantially continuous, thermally insulative, water-impermeable material adapted to conform closely to the shape of a kidney.

* * * * *